(12) United States Patent
von Hoffmann et al.

(10) Patent No.: US 8,292,937 B2
(45) Date of Patent: Oct. 23, 2012

(54) THERAPEUTIC PACK

(75) Inventors: Kristen L. von Hoffmann, Montclair, NJ (US); Eric W. von Hoffmann, Montclair, NJ (US); Diana von Hoffmann, Montclair, NJ (US)

(73) Assignee: Hometown Sports, LLC, Montclair, NJ (US)

( * ) Notice: Subject to any disclaimer, the term of this patent is extended or adjusted under 35 U.S.C. 154(b) by 1309 days.

(21) Appl. No.: 12/019,246

(22) Filed: Jan. 24, 2008

(65) Prior Publication Data
US 2008/0140166 A1    Jun. 12, 2008

Related U.S. Application Data

(63) Continuation-in-part of application No. 11/610,712, filed on Dec. 14, 2006, now Pat. No. 8,012,191, which is a continuation-in-part of application No. 10/389,862, filed on Mar. 14, 2003, now abandoned, which is a continuation-in-part of application No. 10/193,778, filed on Jul. 12, 2002, now abandoned.

(51) Int. Cl.
*A61F 7/00* (2006.01)

(52) U.S. Cl. .......................................... 607/114; 607/96

(58) Field of Classification Search .................. 607/108, 607/112, 114, 96
See application file for complete search history.

(56) References Cited

U.S. PATENT DOCUMENTS

| | | |
|---|---|---|
| 3,596,713 A | 8/1971 | Katz |
| 4,044,773 A | 8/1977 | Baldwin, III |
| 4,104,883 A | 8/1978 | Naef |
| 4,327,447 A | 5/1982 | Carnaghi et al. |
| 4,505,201 A | 3/1985 | Abele |
| 4,516,564 A | 5/1985 | Koiso et al. |
| 4,530,220 A | 7/1985 | Nambu et al. |
| 4,596,250 A | 6/1986 | Beisang, III et al. |
| 4,628,932 A | 12/1986 | Tampa |
| 4,648,864 A | 3/1987 | Evans et al. |

(Continued)

FOREIGN PATENT DOCUMENTS
EP       0360931 A     4/1990
(Continued)

OTHER PUBLICATIONS

International Search Report dated Sep. 17, 2009, for corresponding International Application PCT/US2009/031439, 3 pages.

(Continued)

*Primary Examiner* — Roy Gibson
(74) *Attorney, Agent, or Firm* — Christopher Paradies; Fowler White Boggs P.A.

(57) ABSTRACT

A therapeutic pack provides effective therapeutic heating or cooling to an area of a body. The therapeutic pack comprises a fabric bag, such as taffeta or a spandex material, and a plurality of therapeutic modules within the bag. In one example, the bag is tubular. In another example, the bag including structurally restrict free movement of the plurality of the therapeutic modules from one section of the bag to another section of the bag. However, the therapeutic modules may be capable of freely moving within the bag relative to one another. The therapeutic modules may include a material that repeatedly provides a prolonged cooling or heating, such as a phase change material, within a durable, impermeable shell, such as a polyethylene shell.

13 Claims, 8 Drawing Sheets

U.S. PATENT DOCUMENTS

| | | | |
|---|---|---|---|
| 4,731,283 A | | 3/1988 | Sakane et al. |
| 4,736,088 A | | 4/1988 | Bart |
| 4,973,647 A | | 11/1990 | Bretches et al. |
| 4,981,135 A | | 1/1991 | Hardy |
| 5,040,557 A | | 8/1991 | Morgan |
| 5,069,208 A | | 12/1991 | Noppel et al. |
| 5,078,128 A | * | 1/1992 | Grim et al. ............ 602/23 |
| 5,190,033 A | | 3/1993 | Johnson |
| 5,275,156 A | | 1/1994 | Milligan et al. |
| 5,314,005 A | | 5/1994 | Dobry |
| 5,395,399 A | * | 3/1995 | Rosenwald ............ 607/108 |
| 5,534,020 A | | 7/1996 | Cheney, III et al. |
| 5,603,727 A | | 2/1997 | Clark et al. |
| 5,628,772 A | | 5/1997 | Russell |
| 5,697,961 A | | 12/1997 | Kiamil |
| 5,709,945 A | | 1/1998 | Lee et al. |
| 5,722,482 A | * | 3/1998 | Buckley ............ 165/10 |
| 5,984,953 A | * | 11/1999 | Sabin et al. ............ 607/114 |
| 6,099,555 A | | 8/2000 | Sabin |
| 6,438,755 B1 | | 8/2002 | MacDonald et al. |
| 6,582,456 B1 | * | 6/2003 | Hand et al. ............ 607/108 |
| 6,610,084 B1 | | 8/2003 | Torres |
| 6,755,852 B2 | * | 6/2004 | Lachenbruch et al. ....... 607/114 |
| 6,916,334 B2 | | 7/2005 | Noonan |
| 7,060,086 B2 | | 6/2006 | Wilson et al. |
| 2001/0006865 A1 | | 7/2001 | Holman |
| 2003/0055475 A1 | | 3/2003 | Rousmaniere |
| 2003/0109911 A1 | * | 6/2003 | Lachenbruch et al. ....... 607/112 |
| 2003/0124278 A1 | | 7/2003 | Clark et al. |
| 2004/0210288 A1 | | 10/2004 | Karapetyan |
| 2007/0055330 A1 | | 3/2007 | Rutherford |

FOREIGN PATENT DOCUMENTS

| | | |
|---|---|---|
| GB | 2226956 A | 7/1990 |
| GB | 2316318 A | 2/1998 |
| GB | 2333708 A | 8/1999 |
| JP | 08-084743 A | 4/1996 |
| KR | 20-0397467 Y1 | 10/2005 |

OTHER PUBLICATIONS

Website of Wikipedia, The Free Encyclopedia: http://en.wikipedia.org/wiki/basic_knitted_fabrics,"Basic Knitted Fabrics", 2 pages.

"Fabrics", Website of IB Sports, LLC, Westerville, Ohio: http://www.icebeams.com/ad%20fabrics.htm, 3 pages.

American Health Products, Freezer Storage Bags, 3 pages, www.ahpc.com.

TEAP Energy, Encapsulation Methods, 1 page, http://www.teappcm.comencapsulation.html.

TEAP Energy, PCM Filled Spheres, Mar. 5, 2003, 2 pages, http://www.mjm-engineering.com/spheres.html.

* cited by examiner

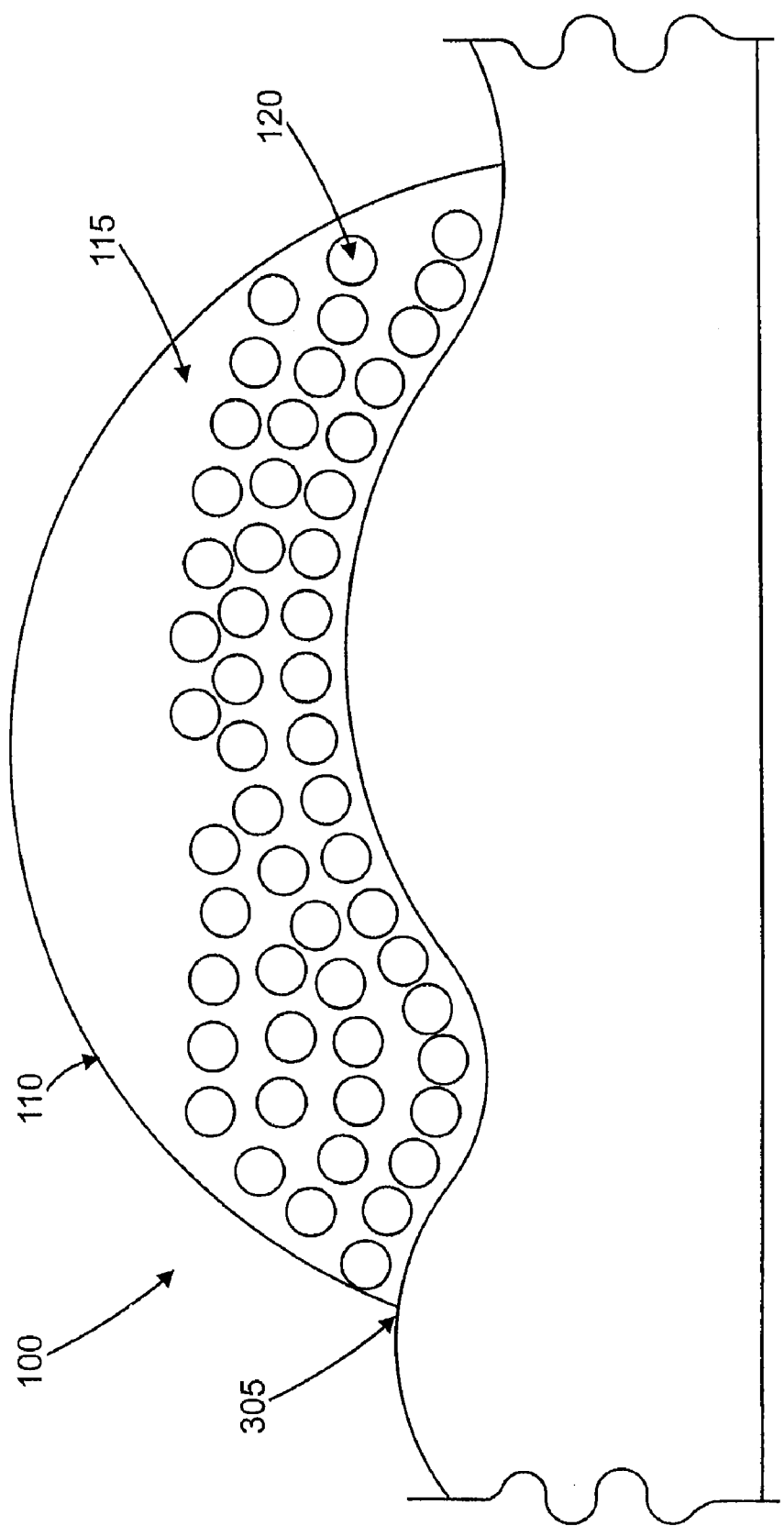

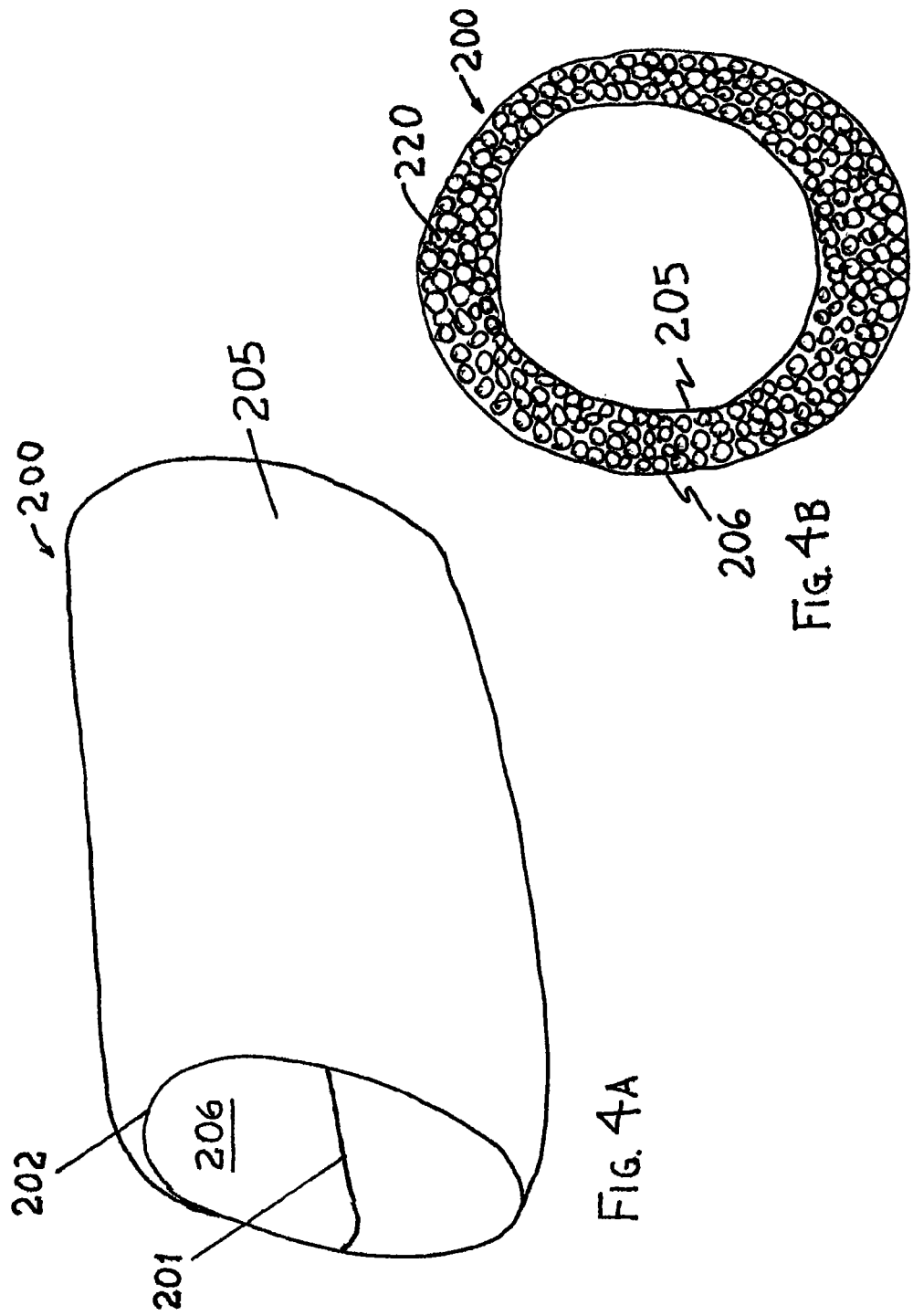

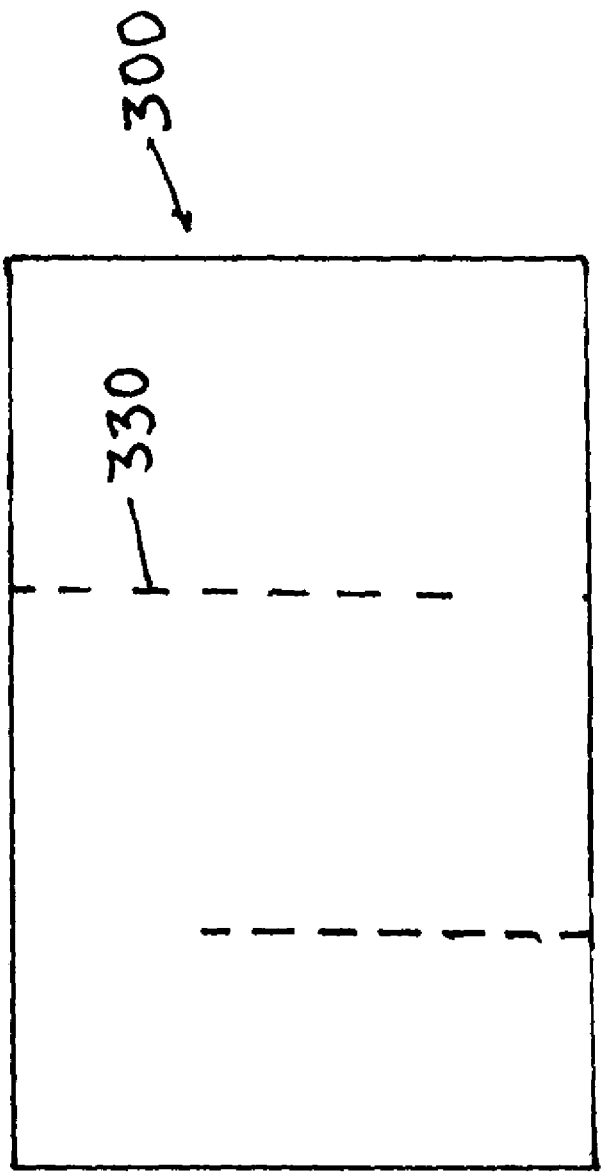

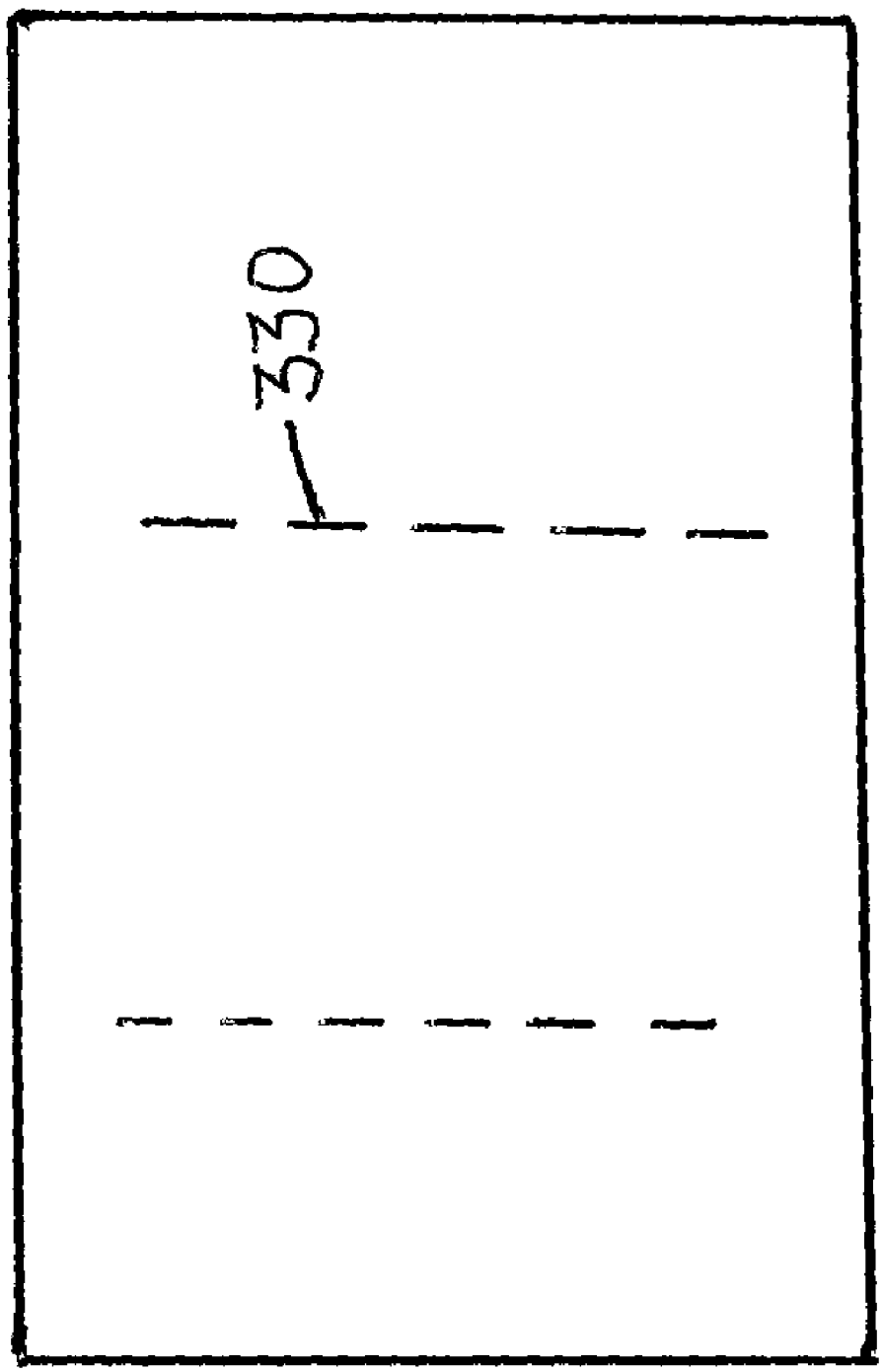

THERAPEUTIC PACK

RELATED APPLICATIONS

The present application is a continuation-in-part application of U.S. patent application Ser. No. 11/610,712, filed Dec. 14, 2006, now U.S. Pat. No. 8,012,191, issued Sep. 6, 2011, which is a continuation-in-part of U.S. patent application Ser. No. 10/389,862, filed Mar. 14, 2003, now abandoned, which is a continuation-in-part of U.S. Ser. No. 10/193,778, filed Jul. 12, 2002, abandoned.

FIELD OF THE INVENTION

The field relates to therapeutic packs, for example, therapeutic packs, used for cooling or heating an area to be subjected to a therapeutic treatment, such as an injured area of a human body.

BACKGROUND OF THE INVENTION

Conventional therapeutic packs may be used to provide a therapeutic treatment to an area of a living body to be subject to a cold or heat treatment. For example, therapeutic packs may be used to treat sports related injuries, by providing a cooling or heating temperature to the injured area.

Ice packs and heat packs are known, but a shortcoming of such packs is the shock to the skin (either cold or hot) when such packs are placed in contact within the skin directly from a freezer or heating unit. It is known to wrap a towel around an ice pack, for example, to prevent the shock of cold, or even skin damage, from occurring during contact with a cold pack. Heat packs may be dangerous and can cause burns on exposed skin. It is known to provide a protective sleeve to place over a heat pack or cold pack, but this requires the sleeve to be located when such a pack is removed from a freezer or heating unit, such as a microwave.

Such packs are also known to freeze into a solid block, requiring striking or crushing forces or a period of waiting in order to allow the phase change materials to separate or become slushy.

U.S. Pat. No. 4,044,773 provides a way of dividing phase change material by striking the bag, for example. The bags used to contain any of these phase change materials is selected to permit such rough handling without spilling the contents. As a result, the packaging does not permit the bag to "drape" as that term is known in the art of fashion.

Herewith, the only materials that are described as having the characteristic of "draping" or the ability to "drape" are comparatively thin fabrics made of woven textiles. Some examples are given of materials that drape, and other examples are given of materials that do not "drape" as that term is defined herein.

For example, plastic films that have adequate strength to serve as bags to contain therapeutic modules are known to not drape. Such sheets are not textiles and are not woven. It is thought, without being limiting that it is necessary to have threads capable of movement, such as in a woven textile, in order to create a fabric that drapes. Some textiles having a thickness not greater than four thousandths of a inch (0.004") are known to drape, such as textiles made of polyethylene, cotton, polypropylene and nylon threads/fibers.

SUMMARY OF THE INVENTION

It is an object of the present invention to improve conventional therapeutic packs by providing a pack design that promotes the cooling or heating effects of the therapeutic pack and better conforms to an area to be subjected to a therapeutic treatment.

It is another object of the present invention to provide a therapeutic pack, which is better suited to provide a cooling or heating temperature to an area to be subjected to a therapeutic treatment.

It is another object of the present invention to provide a therapeutic pack, which does not require a substantial initial deforming force for subdividing a cooling medium, such as ice, into a plurality of smaller particles.

To achieve these objects, an exemplary therapeutic pack according to the present invention includes a container, also referred to herein as a bag, having an interior space and a plurality of therapeutic modules situated in the interior space of the container, in which the therapeutic modules move freely, or at least substantially freely, relative to one another without the need for a substantial initial deforming force.

In this manner, it is believed that the various exemplary therapeutic packs of the present invention may better treat an injury of a living body, for example, a sports related injury of a human body. It is also believed that the therapeutic packs of the present invention provide an advantageous solution for treating injuries in large scale treatment centers, such as hospitals.

One advantage of a fabric bag made of a taffeta or a spandex is that the user does not feel the initial shock of cold (i.e., freezer shock) even without using a towel or barrier and the pack prevents freezer burn, even if the bag is applied to bare skin directly after removing the bag from the freezer. Another advantage is that the bag drapes on the body, covering a larger surface area. Yet another advantage of a spandex fabric is that the stretchable material better conforms to the body, even when the bag is full of therapeutic modules. Still another advantage of a lightweight spandex is that the bag not only conforms and remains in place without slipping but also grips the body part holding the bag in place. Also, the fabric does not sweat as plastic sheet does.

Another advantage of a tubular therapeutic pack is that the pack is stretchable and remains in position when a limb or other body part is inserted into the tube formed by an inner sleeve of the pack. Yet another advantage is that the inner and outer sleeve are reversible, allowing the pack to be easily rolled onto a limb. Yet another advantage is that the selection of a material, such as a spandex, a thickness or gauge, and an elasticity is capable of providing both thermal therapy and a therapeutically effective compression therapy.

BRIEF DESCRIPTION OF THE DRAWINGS

FIG. 3 is a diagram showing application of an exemplary therapeutic pack.

FIGS. 4A and 4B illustrate an example of a tubular therapeutic pack.

FIG. 5A depicts an example of a therapeutic pack with baffles.

FIG. 5B illustrates an example of a baffle regulating movement of the modules.

FIG. 5C depicts another example of baffles regulating movement of the modules.

DETAILED DESCRIPTION

The examples described and the drawings rendered are illustrative and are not to be read as limiting the scope of the invention as it is defined by the appended claims.

Figure 1:
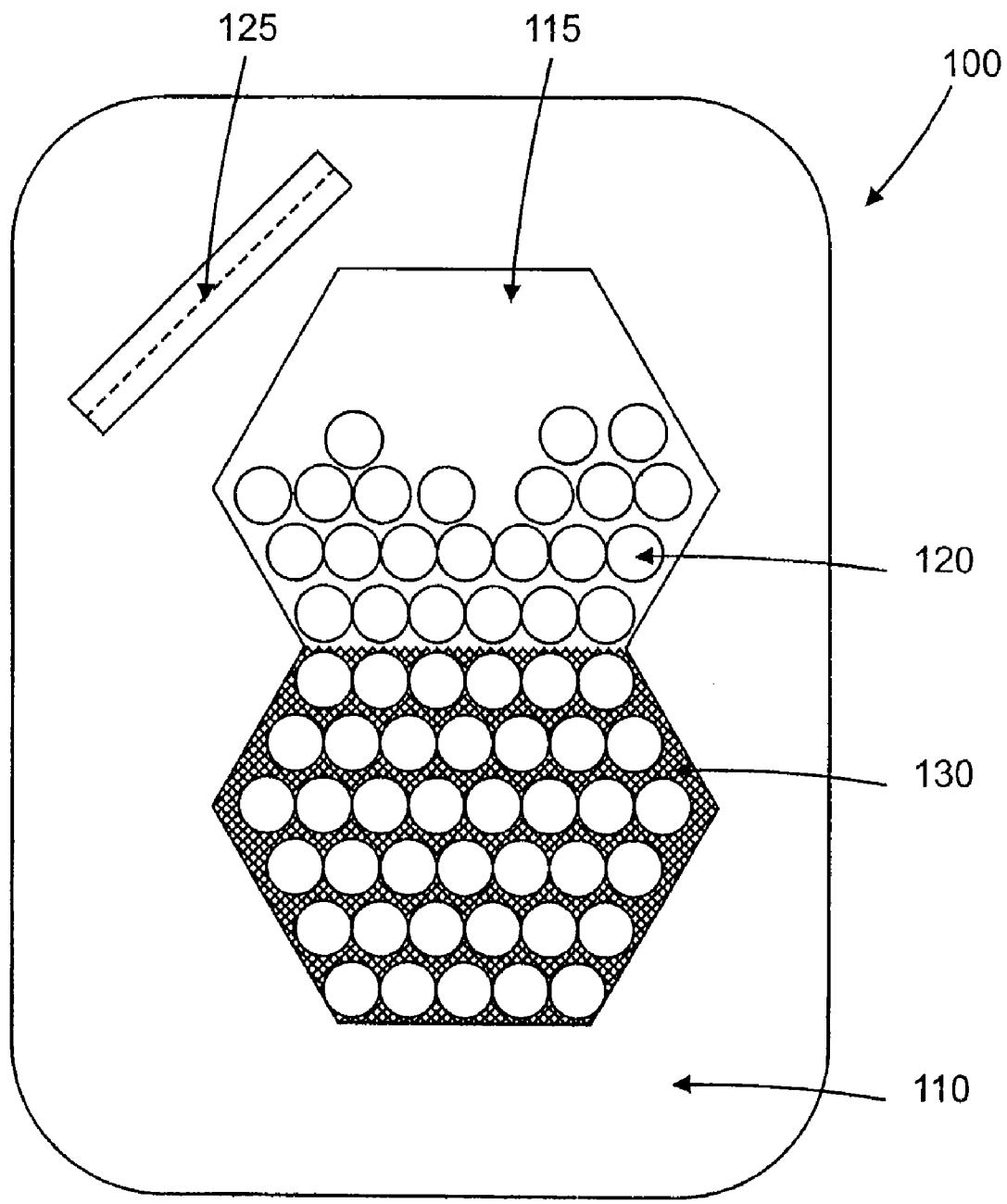
FIG. 1 is a cut-away view showing a first exemplary therapeutic pack.

Referring now to FIG. 1, there is seen a cut-away view of a first exemplary therapeutic pack 100 according to the present invention. As shown in FIG. 1, the therapeutic pack 100 includes a bag 110 having an interior space 115 and a plurality of therapeutic modules 120 situated within the interior space 115 of the bag 110. For example, the bag 110 may include more than 1000 spherical therapeutic modules 120. In one specific embodiment, each spherical therapeutic module has a diameter of between about 11/32 inches and 13/32 inches and each weighing, for example, between about 0.4 grams and 0.6 grams. A volume less than one cubic inch, more preferably less than 0.4 cubic inches is preferred for each module, allowing many modules to conform directly to the body surface. The bag 110 may weigh, for example, about 454 grams when filled with the therapeutic modules 120, depending on the size of the bag and number and volume of therapeutic modules within.

The bag 110 may be made of a strong, durable material and should have a suitable thickness, such that the bag 110 conforms to the area to be subjected to a therapeutic treatment. For example, the material of the bag 110 may have a thickness of less than four thousandths of an inch, such as about three and one half thousandths of an inch (i.e., 3½ mil), where a ???? is used to indicate customary and reasonable manufacturing tolerances.

It is believed that the use of a nylon taffeta in bag 110 is advantageous, since taffeta is less likely to irritate and/or burn the area to be subjected to a therapeutic treatment. It is also believed that taffeta exhibits good conductive properties for conducting the cooling or heating temperature to the area to be subjected to a therapeutic treatment, without causing an ice burn, or cold shock during application of the bag, directly from a freezer, onto bare skin. Reaction to a taffeta or a spandex material has been positive in testing. Comfort and convenience are much greater than expected, while effectiveness is not diminished, provided that therapeutic modules are selected to provide sufficient cooling. Thin, polyethylene module shells are preferred for a lower or higher temperature at the surface of the skin; however, the thickness must be sufficient to prevent extensive rupturing of many of the module shells.

Additionally, the bag 110 may include an antimicrobial and/or antifungal agent to prevent infection. For example, this may reduce the chance of introducing an infectious organism, if the area to be subjected to a temperature treatment includes an open cut and/or abrasion on a human body part. In one embodiment, an antifungal and antimicrobial agent permeates a polyester taffeta bag.

Furthermore, the bag 110 may be designed in any shape, such as oval, square, rectangular, etc. For example, the bag 110 may include a substantially rectangular bag dimensioned, for example, about 6½ inches by 9 inches, having a thickness of about 1¼ inches, when filled with therapeutic modules 120 and laid flat. Many other shapes are possible and some examples are provided.

The bag 110 may permanently enclose the therapeutic modules 120 (i.e., the bag 110 may be a permanently sealed unit) or, as shown in FIG. 1, the bag 110 may include an access apparatus 125, such as a zipper, hook-and-loop tape (e.g., Velcro®), buttons, straps, a twist tie, a slide-lock (e.g., Ziploc®) and/or snaps, operable to permit access to the interior space 115 of the bag 110.[1] In this manner, the therapeutic modules 120 may be replaced if necessary.

[1] Velcro® is a registered trademark of Velcro Industries B.V., Netherlands; Ziploc® is a registered trademark of S.C. Johnson Home Storage, Inc.

In one specific embodiment, the bag 110 is a polyester taffeta. In an alternative embodiment, a portion of the polyester taffeta is lined with a high density polyethylene thin film or some other water impermeable lining. Unlike stiffer materials, polyester taffeta drapes, as that term is used in the fashion industry, meaning that the material easily conforms to the human form under its weight. Other materials may be selected that drape, but many materials are not capable of draping, such as plastic films capable of repeated use and canvas, which are both too stiff to drape effectively. Thus, the term drape is used herein refers only to thin fabrics capable of contacting depressions in a body solely under the force applied by the weight of a single layer of therapeutic modules.

The interior space 115 of the bag 110 between the therapeutic modules 120 may remain devoid of any material, or may include, for example, a filling medium 130, as shown in FIG. 1. The filling medium 130 may include, for example, a gas, such as air or desiccated air, a gelatinous material, a material resistant to expansion when heated (e.g. above 20° C.), a material resistant to freezing when cooled (e.g. below 0° C.) or a chemical substance that generates heat or cold by a chemical reaction or a phase change, for example, without the need for an external cooling or heating source, such as a freezer or heater.

It should be noted that the interior space 115 of the bag 110 between the temperature modules 120 may be completely filled with the filling medium 130 or, alternatively, may only be partially filled with the filling medium 130. In this manner, the bag 110 may permit the filling medium 130 to expand within the bag 110 while freezing or heating, without rupturing the bag 110. Also, each shell 205, as shown in FIG. 2, may enclose less than its full volume of a therapeutic medium 210, allowing for expansion of the therapeutic medium 210.

A preferred filling medium 130 is air, which makes the bag inexpensive to produce and allows for the use of a fabric bag without any liner or film. Thus, the fabric of the bag 110 may be selected from fabrics that drape, for example.

Figure 2:
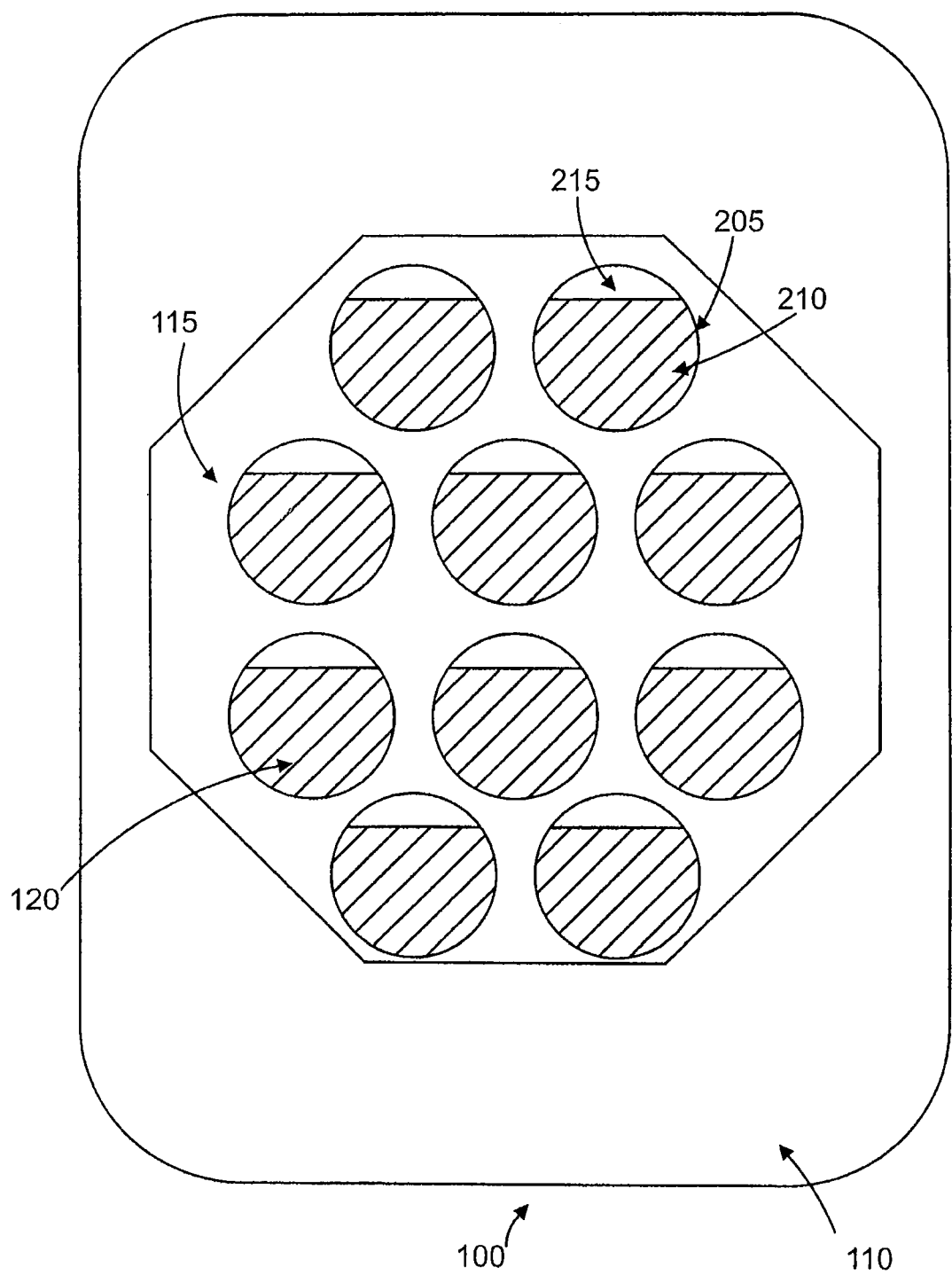
FIG. 2 is a cut-away view showing further detail of the temperature modules shown in FIG. 1.

FIG. 2 shows a cut-away view having greater detail of one embodiment of the therapeutic modules 120. The therapeutic module 120 may include a shell 205 and a therapeutic medium 210 situated within an interior space 215 of the shell 205. The shell 205 may be any shape, for example, substantially spherical, oval, cubic, irregular, etc. In an alternative embodiment, the therapeutic module may be a solid therapeutic medium. In this alternative, the therapeutic medium 210 is a material that has a large heat capacity or undergoes a chemical reaction or solid-solid phase change, for example.

The therapeutic modules 120 may be dimensioned, for example, to be approximately equal in volume or to be two or more different volumes to more densely fill the bag. In one preferred embodiment, each module 120 has a volume less than 0.4 cubic inches. Thus, the therapeutic pack 100 conforms to contours of the area to be subjected to a therapeutic treatment, more effectively promoting uniform application of heating or cooling, for example, as well as reducing the likelihood that the therapeutic pack 100 will slip off the area to be subjected to the therapeutic treatment. The embodiment illustrated in FIGS. 4A, 4B, 6A-6C are capable of elastically fitting around an area to be treated, for example. Further, since the individual therapeutic modules 120 may be small relative to the bag 110 and move substantially freely to one another, at least some of the therapeutic modules 120 may come to rest in an area of the therapeutic pack 100 adjacent to at least a portion of the area to be subjected to a thermal treatment. In this manner, more of the therapeutic modules 120 may individually contact the portion of a body needing treatment, thereby promoting a more effective treatment.

It should be noted that, although FIGS. 1-3 show the therapeutic modules 120 having approximately equal sizes, the therapeutic modules 120 may be of varying sizes and/or shapes, permitting the therapeutic pack 100 to better conform to the contours of the area to be subjected to the temperature treatment and/or better promote the therapeutic effect of the therapeutic pack 100. Furthermore, a volume less than 0.4 cubic inches and/or a diameter of spherical modules less than about 0.5 inches is preferred, because this allows more direct contact of the modules with the area to be treated. However, the size of the modules comprising a shell are preferably large enough to contain a volume of phase change material capable of providing at least 10 minutes of thermal treatment.

The module shell 205 may be of any material operable to contain the therapeutic medium 210, for example, a rigid plastic, a flexible plastic, a sponge-like material, a composite material, an elastomeric material, a non-organic material, an organic material, or a synthetic material may be used. A shell of polyethylene or polypropylene is preferred for encapsulating phase change materials. Polypropylene is preferred for phase change materials having a phase transition of greater than 20° C. Polyethylene is preferred for low temperature phase change materials, having a phase change at less than 1° C.

The therapeutic medium 210 may include any material operable to provide a therapeutic treatment to the body such as heat or cold therapy. For example, the therapeutic medium 210 may include a liquid, a solid, and/or a gelatinous material. For example, the therapeutic medium 210 may be a phase change material, such as water, which provides therapeutic cooling to an area of the body during melting from its frozen state to its liquid state. The therapeutic pack 100 may provide repeated therapeutic treatment by refreezing the liquid water, for example, in a freezer compartment. Water is a convenient phase change material, because it undergoes a phase change at 0° C., a temperature easily achieved in an ordinary freezer compartment.

Also, water has a large heat of fusion, which provides prolonged cooling of the area of the body undergoing treatment, and water is non-toxic. Thus, water is safe and effective. Other phase change materials are known that are also safe and effective. For example, phase change materials (PCM) are available having a range of phase transition temperatures from −31° C. to 90° C., such as the materials offered by TEAP Energy and other firms.

In addition to or in lieu of a liquid, the temperature medium 210 may include, for example, a chemical cooling or heating agent operable to provide the cooling or heating temperature via a chemical reaction, without the need for being externally cooled or heated.

It should be noted that the interior space 215 of the shell 205 may be completely filled with the temperature medium 210 or, alternatively, only be partially filled with the temperature medium 210. Partially filling the shell 205 with the temperature medium 210 may permit the temperature medium 210, for example, liquid water, to expand within the module container 205 while freezing or heating, without rupturing the shell 205.

It should also be noted that, although FIG. 2 shows the shell 205 filled with the temperature medium 210, the interior space 215 of the module container 205 may alternatively be filled with air or be devoid of any temperature medium 210 whatsoever. Alternatively, the temperature 210 may be a solid that has the same composition as the shell, such as a material with a high heat capacity, creating a solid therapeutic module 120. Preferably, the temperature medium 210 is comprised of water and may include a salt and/or thickening agent that is non-toxic, which allows low cost production of modules 120 that provide cooling for an extended period within their phase change temperature range. For pure water, a freezing point of 0 is maintained during thawing within the modules 120. Salts are known to suppress this temperature further to a lower temperature for the initiation of melting.

Referring now to FIG. 3, there is seen a diagram showing an example of a therapeutic pack 100 according to the present invention. When applied to an area to be subjected to a cold or heat treatment 305, for example, an injured portion of the human body (e.g., a human knee), the therapeutic modules 120 of the therapeutic pack 100 move substantially freely relative to one another, even if the therapeutic pack 100 is applied immediately after being removed from a cooling source, such as a freezer. In this manner, the therapeutic modules 120 conform to the area to be subjected to a temperature treatment 305, without the need for a subdividing deforming force and without the need, for example, to wait for the therapeutic pack 100 to at least partially thaw.

Further, it is believed that the ability of the therapeutic pack 100 to conform to the area treated 305, helps the therapeutic pack 100 to stay on any area to be treated, for example, the injured portion of the human body. In addition, a bag 110 of a material that drapes under the weight of the therapeutic pack 100 itself allows the therapeutic medium to come to rest adjacent to the entire surface to be treated, including reentrant curvature on the surface, depending on the size and shape of each of the plurality of therapeutic modules 120.

In still another example, a spandex material is used. For example, Lycra,® is a brand name of stretchable fibers used in spandex fabrics in which the fiber-forming substance is a long chain synthetic polymer comprised of at least 85 percent of a segmented polyurethane.[2] For example, the spandex material may be a blend, such as a 82% nylon and 18% spandex tricot material. The blend of nylon spandex tricot allows lengthwise and crosswise stretch in the bag. In addition, the blend allows the bag to conform readily to the complex curves of the human body. The blend also allows the bag to absorb less water than a bag having material made of cotton. Yet another feature of such a bag is that it is very resistant to runs or tearing.

In one preferred embodiment, an 82% nylon and 18% spandex tricot fabric is selected having a fabric density of about 200 grams per square meter (200 g/m$^2$). This preferred embodiment provides excellent reusability of the therapeutic bag through a multitude of freeze/thaw cycles, while allowing the material to breath and to drape over an area of the body. Furthermore, a bag made in a tubular form of this weight and elasticity is capable of providing a therapeutically effective compression to the area of the body to which it is applied. Simultaneously provided thermal and compressive treatment effectively is an unexpected advantage of a tubular or other form fitting shape for a bag made of spandex, for example. Furthermore, the feel of the material on the skin when applied immediately after removal from a freezer is comfortable, avoiding a sensation of freezer shock. Plastic films of any kind cause an uncomfortable chill to the skin if applied directly without a barrier material between the film and the skin. A barrier material shows the application of cooling therapy and reduces its effectiveness.

A therapeutic pack formed in the shape of a tube has some advantages over a non-tubular geometry. As shown in FIG. 4A, a therapeutic pack is tubular and includes a bag 200 and therapeutic modules 220, which is depicted in a cross-sectional view in FIG. 4B. The therapeutic pack of this example includes an outer sleeve 205 and an inner sleeve 206. A seam 201 joins to ends of a fabric material to form an inner sleeve 206. An additional seam 202 is shown, joining the inner sleeve 206 and the outer sleeve 205. In FIG. 4B, therapeutic modules 220 are illustrated within a space defined between the inner sleeve 206 and the outer sleeve 205. The inner sleeve and the outer sleeve may be of a spandex tricot blend. In one specific example, the spandex tricot blend consists of about 82% nylon and 18% spandex tricot. The terms inner sleeve 206 and outer sleeve 205 are used merely descriptively in conjunction with the drawings of a tubular bag 200. In fact, these two sleeves 206, 205 are completely reversible. Indeed, a method of using the bag on an appendage, such as an arm or leg, allows the bag to be "rolled" onto the appendage such that the inner sleeve 206 becomes the outer sleeve as the outer sleeve 205 becomes the inner sleeve. It has been found that rolling the sleeve onto an appendage is a preferred method of use compared to sliding the bag over an appendage. Rolling reduces pain to an injured portion of a limb, for example. Especially when a spandex material is used, a tubular bag remains in place on an appendage, allowing the person being treated to move about during treatment. In addition, elasticity of the bag may provide a therapeutic compression.

In one example, a plurality of therapeutic modules move freely within a fabric bag such that at least a plurality of the plurality of the therapeutic modules directly contacts the fabric of the bag as the bag contacts an area of the body. The fabric bag may be of a taffeta or a spandex material. Periodically, a person receiving treatment may "shuffle" the modules to bring new, colder modules in contact with the bag.

As shown in the example of FIG. 5A, the therapeutic pack 300 may include baffles 330. Baffles 330 assist in restricting the free movement of therapeutic modules 320. As illustrated in FIG. 5B, for example, baffles may partially close one portion of the interior of the bag from another portion of the interior of the bag such that the free movement of therapeutic modules is partially restricted. Thus, some of the modules may be redistributed to one of the other sections to provide additional cooling there, but other modules may be retained by the baffles from freely moving from one section to another. FIG. 5C illustrates another example of a therapeutic pack 301 with baffles 330 that allow movement of modules 320 around either end.

In one example, baffles 330 prevent movement of the therapeutic modules 320 unless the modules move around the barriers. The baffles 330 may be of any shape, so long as it restricts free movement of the therapeutic modules in some manner. For example, the baffles 330 are depicted in the drawings as stitching through two surfaces of the bag that closes a portion along the width of the bag. In one example, an area of the stitched portion is greater than an unstitched portion along the width of the bag. This unstitched portion remains open, allowing movement of the therapeutic modules through the unstitched portion. However, the length of the stitched portion is selected to substantially restrict movement of the modules through the unstitched portion unless a person assists the modules to move through the unstitched portion.

Figure 6A:
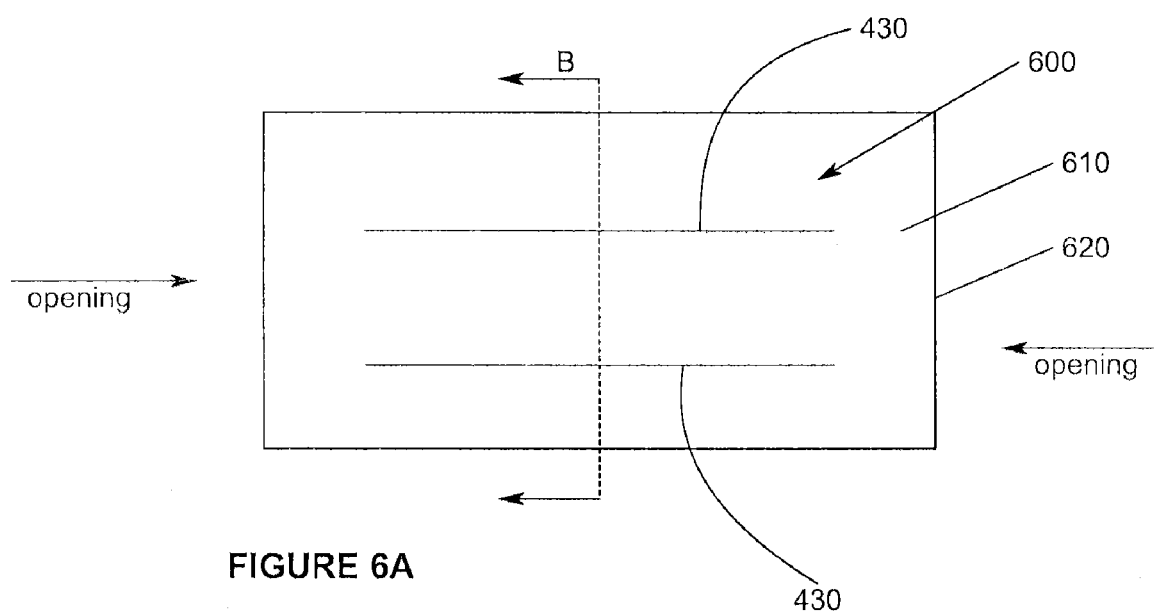
FIGS. 6A-C show an example of a tubular therapeutic pack with baffles.
Figure 6B:
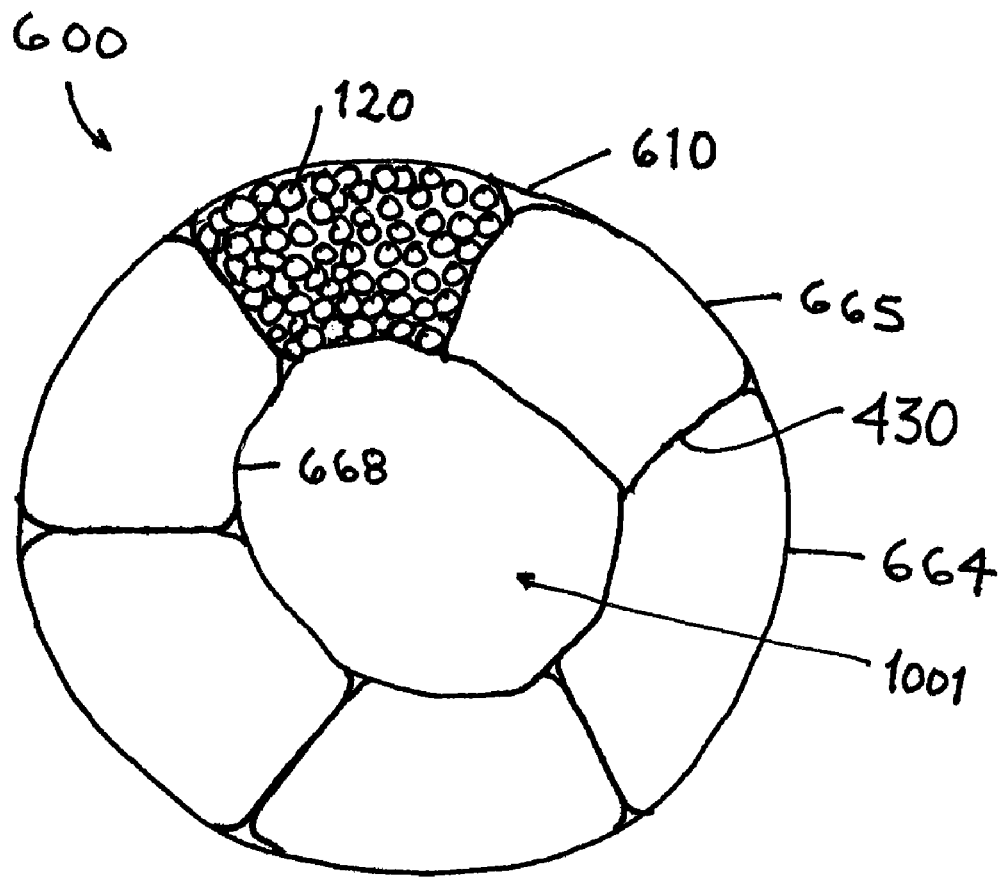

In another example, of a tubular bag or cuff, baffles or barriers are provided such that a user may shuffle therapeutic modules 120 to concentrate a larger number of the modules 120 over an area to be treated, as illustrated in FIGS. 6A and 6B. The baffles 430 divide portions of a cuff 600, such that the movement modules 120 is restricted. Modules may be moved through an opening 610 left along a portion of the baffle or between a baffle and a closed end 620 of the cuff 600. Two baffles 430 are shown in the view of FIG. 6A, but a plurality of baffles 430 may be provided radially disposed and extending longitudinally on a cuff 600, as illustrated in FIG. 6B.

Figure 6C:
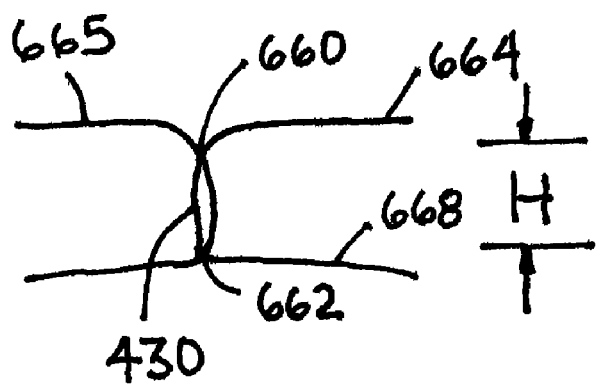

The barriers 430 may be any shape or size, may be continuous or discontinuous, and may be straight, sinusoidal, steps, or arcuate, for example. FIG. 6C shows a detailed view of a barrier 430 having a height H formed by a first length of stitching 660 joining a first section 664 to a second section 665 and a second stitching 662 joining the first section 664, the second section 665 and an inner sleeve 668 of the cuff 600.

Alternative combinations and variations of the examples provided will become apparent based on this disclosure. It is not possible to provide specific examples for all of the many possible combinations and variations of the embodiments described, but such combinations and variations may be claims that eventually issue.

What is claimed is:

1. A tubular therapeutic pack, comprising:
   a bag comprised of an outer sleeve and an inner sleeve joined to the outer sleeve such that an enclosed volume is formed between the outer sleeve and the inner sleeve and the bag forms a tubular body, and a material is selected for the outer and the inner sleeve such that the tubular body is stretchable elastically; and
   a plurality of therapeutic modules are contained in the enclosed volume, such that the plurality of therapeutic modules move substantially freely relative to one another, the plurality of therapeutic modules each comprising a shell and a phase change material contained within the shell wherein the material of the inner sleeve is selected to be a spandex and a plurality of the plurality of therapeutic modules are in direct contact with the spandex.

2. The tubular therapeutic pack according to claim 1, wherein the material of the outer sleeve is selected to be a spandex.

3. The tubular therapeutic pack according to claim 2, wherein the material of the inner sleeve and the outer sleeve are of a spandex having a thickness and elasticity such that the bag provides a therapeutically effective compression, when a limb is inserted through the tubular body.

4. The tubular therapeutic pack according to claim 3, wherein the spandex of the inner sleeve and the outer sleeve is of a spandex tricot.

5. The tubular therapeutic pack according to claim 4, wherein the spandex of the inner sleeve and the outer sleeve consists essentially of a blend of 82% nylon and 18% spandex tricot.

6. The tubular therapeutic pack according to claim 5, wherein the spandex of the inner sleeve and the outer sleeve has a density of about 200 grams/square meter.

7. The tubular therapeutic pack according to claim 1, wherein the phase change material undergoes a phase transition at a temperature less than 1° C.

8. The tubular therapeutic pack according to claim 1, wherein the bag includes at least one baffle partially separating one portion of the enclosed volume from another portion of the enclosed volume such that the free movement of the plurality of therapeutic modules from the one portion to the another portion is at least partially restricted.

9. The tubular therapeutic pack according to claim 8, wherein the at least one baffle is a plurality of baffles and each of the plurality of baffles comprise a stitched portion extending along a length of the bag and the length of the stitched portion is greater than a length of an unstitched portion of the bag, and the unstitched portion of the bag remains open to movement of therapeutic modules from the one portion of the enclosed volume to the another portion of the enclosed volume.

10. The tubular therapeutic pack according to claim 1, wherein the shell of the therapeutic module is of a low density polyethylene.

11. The tubular therapeutic pack according to claim 10, wherein the module shell has an outer diameter of between about 11/32 inches and 13/32 inches.

12. The therapeutic pack according to claim 1, further comprising an antifungal agent or an anti-microbial agent incorporated in the fabric of the bag, the module shell, or both thereof.

13. The therapeutic pack according to claim 12, wherein the anti-microbial agent is incorporated in the module shell.

* * * * *